United States Patent [19]
Renow et al.

[11] Patent Number: 5,484,281
[45] Date of Patent: Jan. 16, 1996

[54] SHOWERHEAD TOOTH CLEANSING APPARATUS

[76] Inventors: Alex Renow; Barry S. Renow, both of 49 Bobwhite La., Hicksville, N.Y. 11801

[21] Appl. No.: 215,049

[22] Filed: Mar. 21, 1994

[51] Int. Cl.$^6$ ..................................... A61G 17/02
[52] U.S. Cl. .................. 433/80; 601/162; 601/165
[58] Field of Search ................... 433/80, 82, 216; 601/162, 165; 15/28, 29

[56] References Cited

U.S. PATENT DOCUMENTS

| | | | |
|---|---|---|---|
| 3,039,123 | 6/1962 | Brucker et al. | 15/28 |
| 3,468,306 | 9/1969 | Heitzman | 601/165 |
| 3,610,234 | 10/1971 | Oates | 601/165 X |
| 3,747,595 | 7/1973 | Grossan | 601/162 X |
| 3,809,977 | 5/1974 | Balamuth et al. | 433/119 X |
| 4,337,040 | 6/1982 | Cammack et al. | 601/162 X |
| 4,564,005 | 1/1986 | Marchand et al. | 601/165 |
| 4,793,331 | 12/1988 | Stewart | 601/165 |
| 5,027,798 | 7/1991 | Primiano | 601/165 |
| 5,095,893 | 3/1992 | Rawden, Jr. | 601/165 |
| 5,220,914 | 6/1993 | Thompson | 601/165 X |

*Primary Examiner*—Nicholas D. Lucchesi

[57] ABSTRACT

A shower mounted dental hygiene device is provided, which consists of a multipurpose direction valve to direct water flow to a shower head, dental hygiene device or both, a pulsating device, a dentifrice introduction device and an erogdynamically designed handle having a quick attachment device for interchanging dental hygiene attachments.

17 Claims, 2 Drawing Sheets

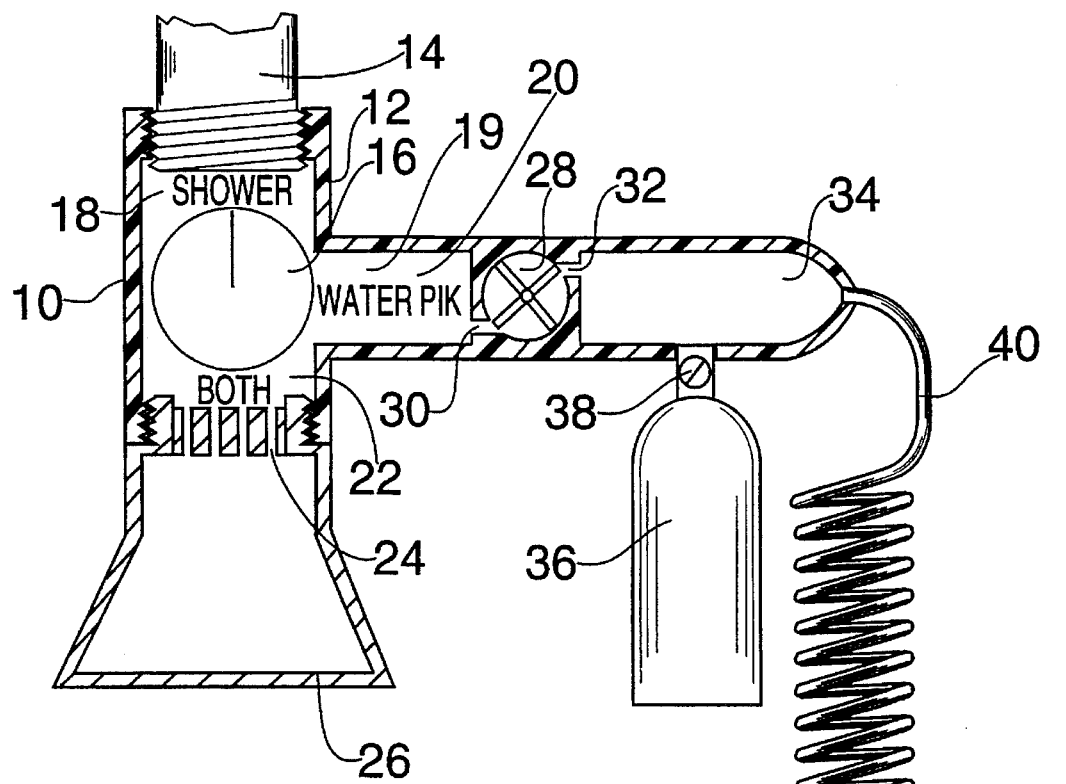
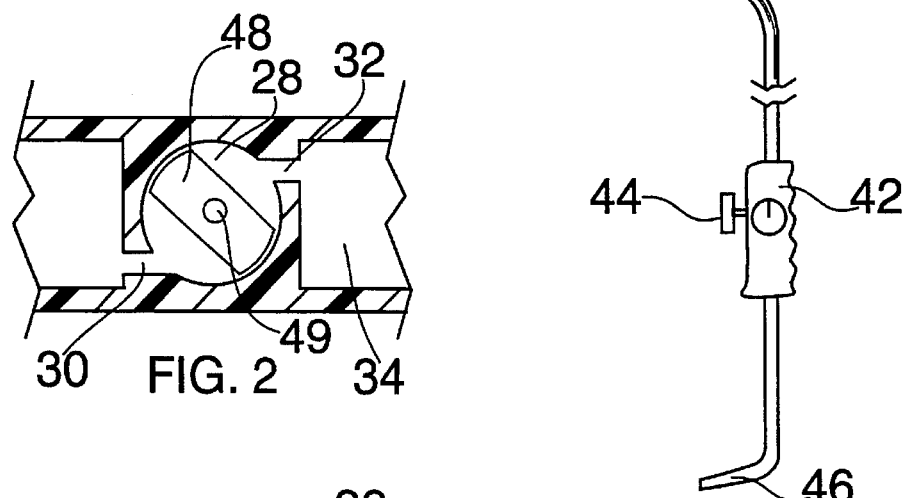
FIG. 2
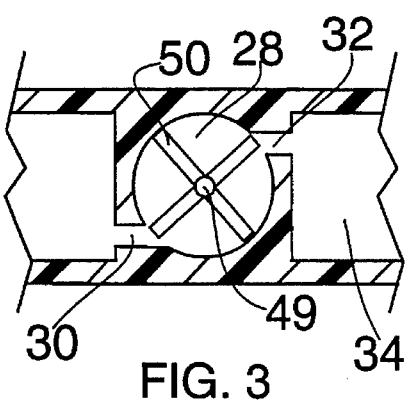
FIG. 3
FIG. 1

SHOWERHEAD TOOTH CLEANSING APPARATUS

BACKGROUND OF THE INVENTION

1. Field of the Invention

The invention relates to a hydraulic apparatus for bodily care, in particular for oral care.

This invention pertains to an apparatus for therapeutically caring for the teeth and gums. The apparatus includes a hydraulic pressurized pik or hydraulic pressurized toothbrush and a dentifrice reservoir which can be adjusted with respect to flow rate or turned off when not in use. The dentifrice reservoir further comprises fortified container enclosure which strengthens the reservoir, allowing the user to grip the container easily to add more dentifrice.

This invention further relates to subject matter of special concern to gum and tooth irrigation appliances, although it has been recognized that many of the improvements in appliances for that field also find useful application in other areas such as the medical cleansing of wounds or cavities.

The present invention relates to a system devised for treating periodontal disease. More particularly, it relates to a hand-held device in the nature of a hydraulic pik or hydraulic toothbrush which may be used by a lay person in his home or on his travels to conduct a course of antisepsis and maintenance treatment of that disease.

2. Description of the Prior Art

Many people are afflicted with periodontal disease, i.e., gingivitis and periodontitis. The most common symptoms of periodontal disease are gingival and alveolation known as plaque which causes deepening of the normal gingival crevice, leading to gum recession and deep gingival pockets. Bacterial inflammation is the main cause of these conditions. These pockets then retain more food and bacteria in their base, where the pathology develops, which pockets are not reachable for cleaning by ordinary means, and the trapped food debris becomes growth medium for bacteria. This then perpetuates the septic, inflammatory process and extends the pathology so that as pockets get deeper, the alveolar bone dissolves, pus extrudes, and the teeth become loose. This is a condition commonly known as pyorrhea.

Additionally, some commercial pulsating devices, such as that sold under the trademark "Water-Pik",™ intended to dislodge food debris between teeth and massage the outer surface of the gums, may be unsuitable for periodontal treatment because they do not supply sufficient water pressure and may not induce antiseptic, anti-inflammatory and other treatment effects. Their effect in the periodontal pocket, if any, is extremely short lasting. Thus, the patient is left without recourse to home therapy and must rely upon course after course of painful dental surgery and curettage and further progress of the disease.

Dental hygiene devices include means for spraying the oral cavity are well known. In particular, U.S. Pat. No. 5,062,795 entitled "Therapeutically Caring for the Mouth and Throat" issued on Nov. 5, 1991 to Woog whose disclosure is incorporated herein by reference, discloses a method and apparatus for moisturizing and therapy of the mouth and throat. A nebulized fine pulsating spray of relatively small droplets is applied. The pressure and temperature of the spray are controlled to obtain optimum penetration. A liquid pulse generator and moisturizing break-up nozzle are employed by the apparatus of this reference.

All of the foregoing patents involve the delivery of water in pulses with a degree of control of some characteristic such as pressure. Usually, pressure control was included in the base unit. As will be observed, there have been some suggestions of placing it in the user's handpiece, so that the user could achieve that control without removing the handpiece from his mouth when it was still delivering liquid. An alternative was to employ a second hand in an inconvenient manner while at the same time collating coordination.

DESCRIPTION OF THE PRIOR ART

The following prior art patents have been found to be relevant to the field of the present invention:

An apparatus and method for removing a coating of undesirable material from a substrate of desired material by impacting the coating with narrowly focused streams of fluid discharged at high velocity from nozzle tips rotated rapidly by a nozzle head and the coated substrate. The nozzle head may be rotated by a motor or self-actuated by tilting the tips out of the plane of the spin axis. The nozzle tips also may be canted radially to undercut and peel away the coating. The nozzle assembly may be continuously or intermittently actuated, fixedly or movably mounted, and used singularly or in plural array. Specific applications are described for descaling metal, cleaning electrolytic bath deposits from electrodes, and removing resinous materials from metal surfaces.

The hydraulic apparatus comprises a handpiece connected via a pipe to a pump through an outlet orifice of the casing and a liquid reservoir feeding the pump, in the position of non-utilization the handpiece and the pipe rolled up in a spiral are accommodated on a platform. The end of the pipe connected to the outlet orifice of the casing is installed rotationally movably about the axis of the pipe. Preferably, the platform is itself installed on the casing in a movable manner about an axis perpendicular to the plane of this platform, by a turning adapter mounted in the outlet orifice of the casing.

The apparatus is a dental hygiene device for therapeutically caring for the mouth and throat. The liquid reservoir can be turned upside down to encase the liquid driving mechanism and the nozzle for a compact storage position. The sidewalls of the reservoir is undulated so as to provide a convenient way to grip or engage the lid of the reservoir.

A system for cleansing a patient's ear is disclosed. This system contains a control unit, a portable applicator, and a means for modifying the flow of fluid from the device when temperature or pressure limits are exceeded.

The control unit contains a heater, a pump, and control means for maintaining the temperature of the liquid within certain limits, for limiting the pressure of the liquid, and for varying the flow rate of the liquid.

The portable applicator contains a handpiece, a nozzle which is connected to the fluid source and is mounted on the handpiece, and a means for providing a signal to the control unit.

An irrigation appliance uses a reservoir which inverts to form a cover and includes a simplified valve in the reservoir as well as a switching mechanism adapted thereto. Liquid delivered to the unit from the reservoir is controlled as to pressure by adjustment on the hand-held device remote from the unit. In the base unit are elements which regulate forward and backward flow in order to obtain outlet pressure control.

A periodontal pocket irrigating and treatment system includes a dispenser capable of containing a medication. The system enables an individual patient to self-administer a medication or irrigant into periodontal pockets while home or travelling. A housing holds a tube of medication, and a roller squeezes the tube, thereby releasing an incremental portion of the medication therefrom. A control, operable from the outside of the housing, urges the roller in increments along the interior of the housing, squeezing the tube in a controlled fashion. A nozzle is attached to the tube for delivering the medication from the tube through a nozzle end of small diameter to the periodontal pocket. Optionally, a flexible tip is attached to end of nozzle for elimination of pain and for guidance around curvatures of the periodontal pocket. The medication preferably is a gel, but may be in other form, which includes an active medication and a water-soluble carrying agent. In one embodiment, the active medication is contained in micro-pellets in the gel.

The invention discloses various ultrasonic dental equipment primarily adapted to be used for professional dental purposes as well as various dental procedures capable of being performed with the ultrasonic instrumentation. The ultrasonic dental system permits the user to selectively utilize a variety of fluids within the oral hygienic procedures carried out by the dentist. The fluids may be selective medicaments that are pumped through the dental system from either an external source i.e., water, to various other fluids each for its intended usage.

Each of the above described prior art inventions differ from the present invention and are not anticipated nor obvious with respect to the following items singularly and in combination;

a) not adaptable for use and connection in a shower, b) not powered solely by normal household water pressure, c) dentifrice mixing means, d) lightweight hand-held hydraulic pik or hydraulic toothbrush adapters, and e) easily stored for travelling.

Numerous hydraulic pik or hydraulic toothbrush devices have been provided in prior art. While these units may be suitable for the particular purpose to which they address, they would not be as suitable for the purposes of the present invention as heretofore described.

OBJECTS AND SUMMARY OF THE INVENTION

It is therefore an object of this invention to provide an apparatus for dental hygiene which can be reduced in size for storage and travelling.

It is therefore a further object of this invention to provide an apparatus for dental hygiene with a dentifrice reservoir which can be removed for ease in cleaning and addition of dentifrice.

A still further object is to afford the user with a greater degree of convenience in control of the pressure of delivered irrigating water or other dentifrice liquid.

Another aspect of the present invention involves a novel valve for use between such a shower, hydraulic pik or hydraulic toothbrush and dentifrice reservoir.

It is an object of the present invention to provide a device which overcomes the deficiencies of the prior art, and facilitates the home or travelling treatment of patients suffering from periodontal disease.

Another object of the invention is to provide a device which is capable of being conveniently hand held. The device is also hand controlled, and is capable of dispensing predetermined portions of medication or dentifrice into periodontal pockets.

A primary object of the present invention is to provide a dental hygiene device that will overcome the shortcomings of the prior art devices.

Another object is to provide a dental hygiene device in which the device can be easily attached to a shower head.

An additional object is to provide a dental hygiene device in which a fog proof mirror may be mounted to said device to facilitate dental hygiene in the shower.

An additional object is to provide a dental hygiene device whereby additional attachments may be stored.

A further object is to provide a dental hygiene device which has interchangeable attachments such as a toothbrush, pik and razor.

A further object is to provide a dental hygiene device which is hand held and has a push-button type of on/off valve contained within the handle.

A further object is to provide a dental hygiene device that is simple and easy to use.

A still further object is to provide a dental hygiene device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

LIST OF REFERENCE NUMERALS

10—DENTAL HYGIENE DEVICE
12—HOUSING
14—WATER INLET
16—DIRECTOR VALVE
18—FIRST CHAMBER
20—SECOND CHAMBER
22—BOTH HYDRO FLOSS AND SHOWER POSITION
24—SHOWER HEAD SCREEN
26—SHOWER HEAD
28—PULSATOR CHAMBER
30—PULSATOR CHAMBER INLET
32—PULSATOR CHAMBER OUTLET
34—THIRD CHAMBER
36—DENTIFRICE RESERVOIR
38—DENTIFRICE RESERVOIR VALVE
40—HOSE
42—HANDLE
44—SUPPRESSOR VALVE
46—Hydro floss
48—SINGULAR PULSATOR PROPELLER
49—PULSATOR AXIAL
50—DOUBLE PULSATOR PROPELLER
52—RECTANGULAR HEAD TOOTHBRUSH
54—RECTANGLFLAR HEAD HOUSING
56—TOOTHBRUSH BRISTLE HYDRODYNAMIC FINS
58—RECTANGULAR HEAD HOUSING WATER OUTLET
60—WATER FLOW
62—BRISTLES
63—ROUND HEAD TOOTHBRUSH
64—ROUND HEAD TOOTHBRUSH HOUSING
66—CLOCKWISE WATER FLOW 68—COUNTER-CLOCKWISE WATER FLOW
70—INNER ROTATING BRISTLES
72—OUTER ROTATING BRISTLES
74—LOWER WATER FLOW
76—UPPER WATER FLOW
77—WATER FLOW DIRECTING BLOCK
78—OUTER BRISTLES HYDRODYNAMIC FINS
79—INNER BRISTLES HYDRODYNAMIC FINS
80—HYDRO FLOSS OUTLET
82—HYDRO FLOSS HEAD
84—MALE SNAP-ON AND SCREW-IN HOUSING
86—SNAP-ON AND SCREW-IN HOUSING
88—FEMALE SNAP-ON AND SCREW-IN FASTENER
90—SNAP-ON AND SCREW-IN HOUSING STOPPER

BRIEF DESCRIPTION OF THE DRAWING FIGURES

FIG. 1 is a perspective cross-sectional view of a dental hygiene device exhibiting a three-way valve, water pulsator, dentifrice reservoir and hose with an ergonomically designed handle at it's terminus with a dental hygiene apparatus such as a hydro floss attached thereto.

FIG. 2 is a cross-sectional view of one type of water pulsator having a two bladed water pulsating propeller.

FIG. 3 is a cross-sectional-view of a water pulsator having a four bladed water pulsating propeller.

DETAILED DESCRIPTION OF THE PREFERRED EMBODIMENTS

Figure 4:
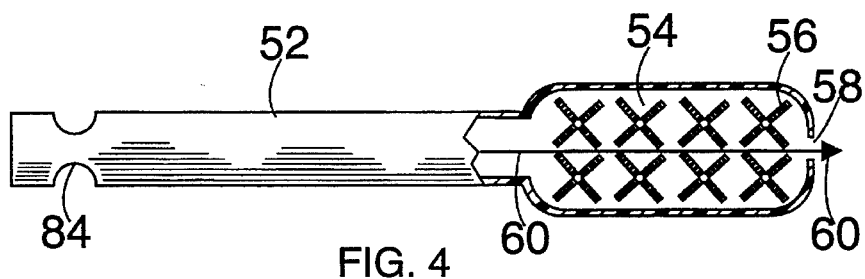
FIG. 4 is a top cross sectional-view of a rectangular head tooth brush having individually rotating propellers connected to bristles.

Referring to FIG. 1, the dental hygiene device 10 is comprised of a housing 12 which can be easily attached to a water source inlet 14 commonly found in most residential and commercial bathrooms. At the opposite distal end from the water inlet 14 of the dental hygiene device 10 is a shower head 26 which is easily attached to the first chamber 18 of the dental hygiene device 10. The shower head 26 has a shower head screen 24 which evenly distributes the water pressure into rain-like droplets. A director valve 16 is positioned within the first chamber 18 with different positions to direct water flow such as hydro floss position 20, shower position 18, and both hydro floss and shower position 22. This feature enables a person using said invention to chose any of the various water flow positions while utilizing said device. When the director valve is positioned in the hydro floss position 20, the water flow is directed from the first chamber 18 to the second chamber 20 and then to the pulsating chamber 28. Due to the geometric configuration of the pulsator chamber 28, the water enters through a pulsator chamber inlet 30 which is diametrically oppositely located from the pulsator chamber outlet 32. Within the pulsator chamber 28 is a means for water pulsation to aid in the effective treatment of oral hygiene while massaging the gums and dislodging food particles between teeth. The pulsator chamber 28 is connected to a third chamber 34 which functions as a mixing chamber to allow the application of dentifrice to the water flow. There is a dentifrice reservoir 36 having a dentifrice reservoir valve 38 to meter dentifrice which is removably attached to the third chamber 34. Located at the distal end of the third chamber 34 is a hose 40 depicted as having a coiling configuration in the drawing which is connected to the handle 42. The handle 42 has a suppressor valve 44 contained therein to easily and rapidly regulate the amount of water flow from the dental hygiene device 10.

Referring now to FIGS. 2 and 3, which graphically depicts different configurations of pulsator chambers 28. One depiction of a pulsator chamber 28 has a singular pulsator propeller rotatably mounted on a pulsator axis 49 as exhibited in FIG. 2 whereas another example graphically represented in FIG. 3 is a multiple bladed pulsator propeller having double pulsator propellers 50.

Figure 9:
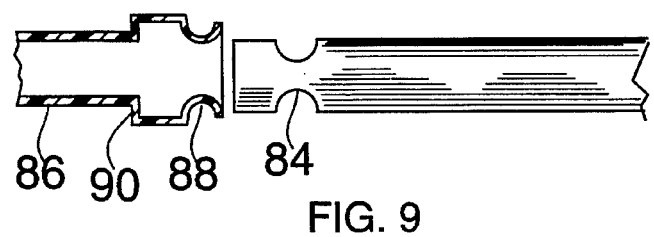
FIG. 9 is a cross-sectional view of a dental hygiene attachment fastening means having a female fastener attached to the ergonomically designed handle and a male fastener attached to the terminal end of the dental fastening means.

Referring now to FIG. 9, the handle 42 has a connecting means to interchangeably attach various dental hygiene devices. The handle 42, has a snap-on [and screw-in] housing 86 which contains a snap-on [and screw-in] housing stopper 90 which functions to align the depth of the insertion of various interchangeable attachments. The snap-on [and screw-in] housing 86 also has a male snap-on [and screw-in] fastener which securely yet easily fastens to a female snap-on [and screw-in] fastener located on the various interchangeable dental hygiene attachments.

Figure 5:
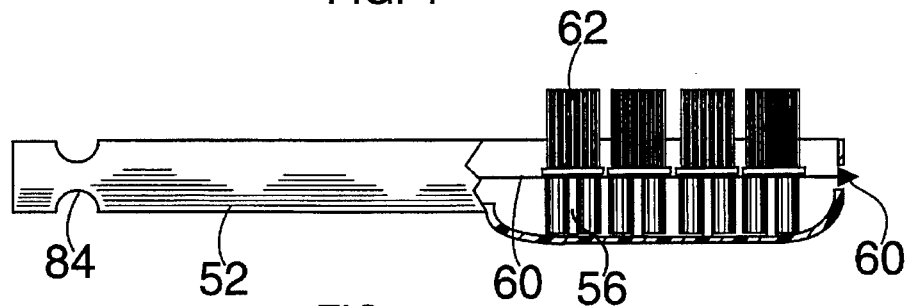
FIG. 5 is a side cross sectional-view of a rectangular head tooth brush having individually rotating propellers connected to bristles.

Referring now to FIGS. 4 and 5, a rectangular head toothbrush 52 has a rectangular head housing 54 containing a plurality of rotatably mounted bristles 62 connected to tooth brush bristle hydrodynamic fins 56. When water flows 60 through the rectangular head housing 54, the pressure of the water rotates the plurality of tooth brush bristle hydrodynamic fins 56 which in turn rotate said bristles 62 functioning to improve oral cleaning. The rectangular head housing 54 has at least one rectangular head housing water outlet which is depicted in these FIGS. 4 and 5 at the distal end. However, another configuration might allow the water pressure to exit through or adjacent to the rotating bristles, thus, improving oral hygiene.

Figure 6:
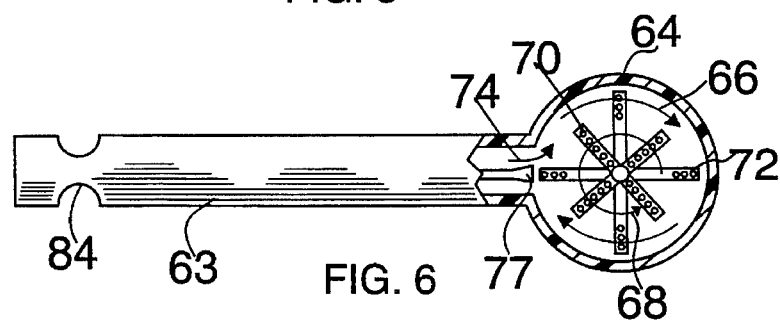
FIG. 6 is a top cross sectional-view of a round head tooth brush having individually counter rotating propellers connected to corresponding individual counter rotating bristle bundles.
Figure 7:
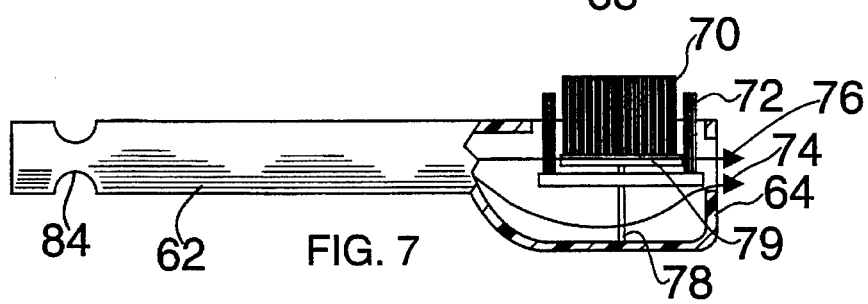
FIG. 7 is a side cross sectional-view of a round head tooth brush having individually counter rotating propellers connected to corresponding individual counter rotating bristle bundles.

Referring to another version of a tooth brush-like attachment as exhibited in FIGS. 6 and 7, round head tooth brush 63 comprising a round head housing 64 having counter rotating inner 70 and outer 72 rotating bristles. The water flow is directed by a water flow directing block 77 in two directions such as a lower water flow 74 which corresponds to a counter-clockwise rotation of the inner rotating bristles 70 by means of the inner bristle hydrodynamic fins 79 and an upper water flow 76 which corresponds to a clockwise water flow 66 which rotates the outer rotating bristles 72 by means of the outer bristles hydrodynamic fins 78.

Figure 8:
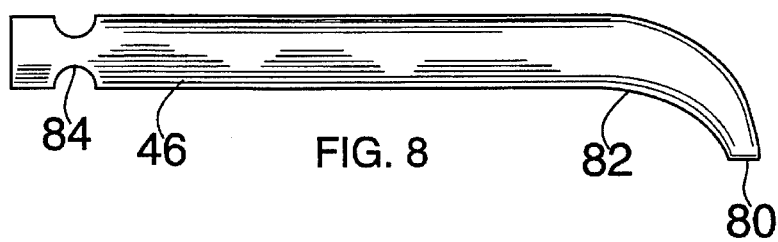
FIG. 8 is a cross-sectional view of a water-pik having a curved tapered top terminating in a narrow spout.

Referring now to FIG. 8 which exhibits a hydro floss 46 having an angled hydro floss head 82 which facilitates insertion of said device into a mouth and improves directional flow of pressurized water flow from the hydro floss outlet 80 which can also be fitted with variable orifices for wider and/or narrower streams of water between teeth to dislodge food particles and plaque.

Referring lastly to FIG. 9 which exhibits a snap-on and screw-in housing 86 which is located at the terminal end of ergonomically designed handle 42 comprising a female snap-on and screw-in fastener 88 and a snap-on and screw-in housing stopper 90. The male snap-on and screw-in fastener 84 easily inserts onto the male snap-on and screw-in fastener 84 forming a watertight snug fit.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letter Patent is set forth in the appended claims:

1. A dental hygiene device comprising:
   a) means for attaching said dental hygiene device to a water outlet commonly found in residential or commercial bathrooms,
   b) a hydrodynamic pulsating means,
   c) a dentifrice reservoir,
   d) a flexible hose,
   e) a handle having quick fastening attachment means for interchanging of dental hygiene attachments,
   f) a counter rotating toothbrush, and
   g) a dental hygiene attachment, said dental hygiene attachment including a toothbrush having a round head configuration comprising an inner set and outer set of individual hydrodnamically driven counter-rotating elements which are directly connected to an inner circular bundle of rotatable bristles rotating in one direction and an outer bundle of rotating bristles rotating in an opposite direction respectively, thus, improving oral cleaning.

2. A dental hygiene device as described in claim 1, wherein said means for attaching has at least one adjustable valve directing water flow to a shower head and dental hygiene attachments.

3. A dental hygiene device as described in claim 1, wherein said means for attaching has an quick fastening attachment means to connect said dental hygiene device to a standard shower head.

4. A dental hygiene device as described in claim 1, wherein said counter-rotating elements further comprising multiple blades rotatably connected to a central axis.

5. A dental hygiene device as described in claim 4, wherein said hydrodynamic pulsating means has at least one water inlet and at least one water outlet diametrically located on opposite sides.

6. A dental hygiene device as described in claim 1, wherein said dentifrice reservoir has a metering valve functioning to regulate the addition of dentifrice to a water flow.

7. A dental hygiene device as described in claim 6, wherein said reservoir is directly connected to a mixing chamber functioning to mix said dentifrice with a water flow.

8. A dental hygiene device as described in claim 1, wherein said flexible hose is coiled.

9. A dental hygiene device as described in claim 1, wherein said quick fastening attachment means further comprises a snap-on and screw-in quick changing means for attaching said handle to said dental hygiene attachments.

10. A dental hygiene device as described in claim 9, wherein said handle has a suppressor valve functioning to facilitate the flow of water from said handle to said dental hygiene attachment.

11. A dental hygiene device as described in claim 10, wherein said dental hygiene devices each have a female snap-on fastener functioning to attach said attachment to said handle.

12. A dental hygiene device as described in claim 11, wherein said female snap-on fastener has an annular concave ting configuration.

13. A dental hygiene device as described in claim 11, wherein said attachment has a male snap-on fastener having an annular convex ring configuration.

14. A dental hygiene device as described in claim 1, wherein said device is constructed from a material selected from the group consisting of copper, plastic, plastic composites, chrome, brass, steel, metal, metal alloys, fiberglass, epoxy, carbon-graphite, ceramic, nylon, and Teflon.

15. A dental hygiene device as described in claim 1, wherein said device is manufactured from a material which is non-corrosive.

16. A dental hygiene device as described in claim 1, wherein said handle is ergonomically designed to fit comfortably in a hand.

17. A dental hygiene device as recited in claim 1, further comprising a plurality of supplemental hygiene attachments.

\* \* \* \* \*